(12) United States Patent
Nuninger et al.

(10) Patent No.: US 7,150,877 B2
(45) Date of Patent: Dec. 19, 2006

(54) FUNGICIDAL MIXTURES COMPRISING R-METALAXYL

(75) Inventors: Cosima Nuninger, Colmar (FR); Martin Weiss, Basel (CH); Andrew John Leadbeater, Aesch (CH)

(73) Assignee: Syngenta Participations AG, Basel (CH)

( * ) Notice: Subject to any disclaimer, the term of this patent is extended or adjusted under 35 U.S.C. 154(b) by 511 days.

(21) Appl. No.: 09/798,181

(22) Filed: Mar. 2, 2001

(65) Prior Publication Data

US 2001/0046492 A1     Nov. 29, 2001

Related U.S. Application Data

(63) Continuation of application No. PCT/EP99/06460, filed on Sep. 2, 1999.

(30) Foreign Application Priority Data

Sep. 4, 1998   (GB) ................... 9819317.0

(51) Int. Cl.
*A61K 36/00*   (2006.01)
*A01N 65/00*   (2006.01)
(52) U.S. Cl. .............. 424/405; 424/725; 424/780; 435/243
(58) Field of Classification Search ............... 424/405, 424/780, 725; 435/243; 514/398, 522, 539, 514/567, 479, 600
See application file for complete search history.

(56) References Cited

U.S. PATENT DOCUMENTS

| | | | |
|---|---|---|---|
| 4,829,085 A * | 5/1989 | Wenderoth et al. | |
| 5,304,572 A * | 4/1994 | Michelotti et al. | |
| 5,348,742 A * | 9/1994 | Howell et al. | |
| 5,637,729 A * | 6/1997 | Lacroix et al. | |
| 5,723,491 A * | 3/1998 | Nuninger et al. | |
| 5,776,976 A * | 7/1998 | Dehne et al. | |
| 5,843,982 A | 12/1998 | Leadbitter | |
| 6,069,171 A | 5/2000 | Young et al. | |
| 6,107,340 A | 8/2000 | Young et al. | |

FOREIGN PATENT DOCUMENTS

| EP | 0 472 494 A | 2/1992 |
|---|---|---|
| EP | 0 741 970 A | 11/1996 |
| EP | 0 935 917 A | 8/1999 |
| WO | WO 93 24467 A | 12/1993 |
| WO | WO 96 01559 A | 1/1996 |
| WO | WO 96 01560 A | 1/1996 |
| WO | WO 96 03044 A | 2/1996 |

OTHER PUBLICATIONS

Phytophthora infestans.*

* cited by examiner

Primary Examiner—Ruth A Davis
(74) Attorney, Agent, or Firm—William A. Teoli, Jr.

(57) ABSTRACT

The present invention relates to novel fungicidal two-component compositions based on metalaxyl having an R-enantiomer content of more than 70% by weight as one essential component and a second fungicidal component, for the treatment of phytopathogenic diseases of crop plants, especially phytopathogenic fungi, and to a method of combating phytopathogenic diseases on crop plants. The metalaxyl component is called active ingredient I.

The following fungicides may be used as the second component II of the mixture:
either a compound IIA
N-(3'-(1'-chloro-3-methyl 2'-oxopentan))-3,5-dichloro-4-methylbenzamide (EP-600629); or
a compound IIB (EP-253213)
methyl (E)-2-methoxyimino-[2-(o-tolyloxymethyl)phenyl] acetate; or
a (S)-valinamide of formula IIC (EP-472996)

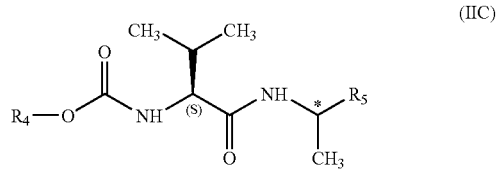

wherein $R_4$ is isopropyl, and
$R_5$ is 4-methylphenyl, and wherein the asymmetric center is preferably (R); or
a compound IID (EP-551048)
(S)-1-anilino-4-methyl-2-methylthio-4-phenylimidazolin-5-one; or
a compound IIE, the *Pseudomonas fluoresens* strain, ATCC accession No. 55169 (U.S. Pat. No. 5,348,742)
is particulary effective in combating or preventing fungal diseases of crop plants. These combinations exhibit synergistic fungicidal activity.

3 Claims, No Drawings

FUNGICIDAL MIXTURES COMPRISING R-METALAXYL

This application is a continuation of international application no. PCT/EP99/06460, filed Sep. 2, 1999.

The present invention relates to novel fungicidal two-component compositions based on metalaxyl having an R-enantiomer content of more than 70% by weight as one essential component and a second fungicidal component, for the treatment of phytopathogenic diseases of crop plants, especially phytopathogenic fungi, and to a method of combating phytopathogenic diseases on crop plants. The metalaxyl component is called active ingredient I.

The following fungicides may be used as the second component II of the mixture:

either a compound IIA

N-(3'-(1'-chloro-3-methyl 2'-oxopentan))-3,5-dichloro-4-methylbenzamide (EP-600629); or a compound IIB (EP-253213)

methyl (E)-2-methoxyimino-[2-(o-tolyloxymethyl)phenyl] acetate; or a (S)-valinamide of formula IIC (EP-472996)

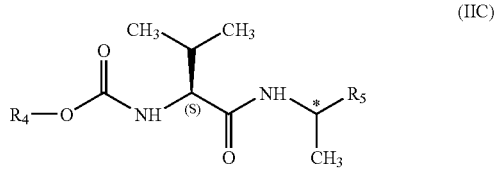

wherein $R_4$ is isopropyl, and $R_5$ is 4-methylphenyl, and wherein the asymmetric center is preferably (R); or a compound IID (EP-551048)

(S)-1-anilino-4-methyl-2-methylthio-4-phenylimidazolin-5-one; or a compound IIE, the *Pseudomonas fluoresens* strain, ATCC accession No. 55169 (U.S. Pat. No. 5,348,742)

is particularly effective in combating or preventing fungal diseases of crop plants. These combinations exhibit synergistic fungicidal activity.

More specifically, the invention relates to mixtures comprising metalaxyl having an R-enantiomer content of more than 85% by weight, preferably of more than 92% by weight, and especially containing pure R-enantiomer that is essentially free of S-enantiomer.

Metalaxyl is methyl N-(2,6-dimethylphenyl)-N-(methoxyacetyl)-DL-alaninate of the formula

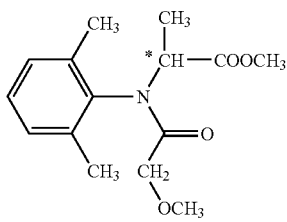

It has an asymmetric *C atom and can be resolved into the enantiomers in customary manner (GB-P-1500581). Since 1975 it has been known to those skilled in the art that the R-enantiomer is far superior to the S-enantiomer in terms of fungicidal action and is in practice regarded as the true mechanism of action. Likewise, mixtures of metalaxyl racemate have become known commercially or otherwise.

It has now been found, completely surprisingly, that R-metalaxyl in pure or more than 70% form, in admixtures with the fungicidal components IIA to IIE, achieves a synergistically enhanced action which in some cases exceeds that of the prior-known mixtures based on the racemate by a factor of 10. Given that half of the racemate consists of R-enantiomer, factors of approximately 2 or, at most, 3 were to be expected.

The component I is known as mefenoxam. The compounds of component II are known in the art with the common names:

IIB kresoximmethyl; IIC iprovalicarb and IID fenamidone.

With this completely unexpected result, the present invention constitutes a very considerable enrichment of the art and represents a possible means of reducing in an environmentally protective manner the total amount of fungicides used for controlling phytopathogen fungi, especially Oomycetes on plants.

The combinations according to the invention may also comprise more than one of the active components II, if broadening of the spectrum of disease control is desired.

The active ingredient combinations are effective against phytopathogenic fungi belonging to the following class: Oomycetes (e.g. *Phytophthora, Peronospora, Bremia, Pythium, Plasmopara*).

Target crops for the areas of indication disclosed herein comprise within the scope of this invention e.g. the following species of plants: cereals (rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, pepper); lauraceae (avocados, cinnamon, camphor); or plants such as maize, tobacco, nuts, sugar cane, tea, vines, hops, durian and natural rubber plants, as well as ornamentals (flowers, shrubs, broad-leaved trees and evergreens, such as conifers or bedding plants). This list does not represent any limitation.

The amount of combination of the invention to be applied, will depend on various factors such as the compound employed, the subject of the treatment (plant, soil, seed), the type of treatment (e.g. spraying, dusting, seed dressing, soil incorporation, stem painting, trunk injection), the purpose of the treatment (prophylactic or therapeutic), the type of fungi to be treated and the application time.

Particularly preferred mixing partners of the compound I are those which comprise as component II a compound IIA or IIC.

Another embodiment of the present invention is represented by those combination which comprise the compound I and as component II a compound IIB, IID or IIE.

It has been found that the use of compound I in combination with the compounds of formula II surprisingly and substantially enhances the effectiveness of the latter against fungi, and vice versa. Additionally, the method of the invention is effective against a wider spectrum of such fungi that can be combated with the active ingredients of this method when used solely. The weight ratio of I:II is so selected as to give a synergistic fungicidal action. In general the weight ratio of I:II is between 10:1 and 1:20. The synergistic action of the composition is apparent from the fact that the fungicidal action of the composition of I+II is greater than the sum of the fungicidal actions of I and II.

Where the component II is the compound IIA the weight ratio is for example between 10:1 and 1:10, especially 5:1 and 1:5, and more preferably 2:1 and 1:2.

Where component II is the compound IIB, the weight ratio is for example between 10:1 and 1:10, especially 3:1 and 1:3, and more preferably 2:1 and 1:2.

Where the component II is a compound of formula IIC the weight ratio is for example between 10:1 and 1:10, especially 3:1 and 1:3, and more preferably 2:1 to 1:2.

Where component II is a compound of formula IID, the weight ratio is for example between 10:1 and 1:10, especially 2:1 and 1:2.

Where component II is the compound IIE, the mixing ratio is for example between 10:1 and 1:10, especially 3:1 and 1:3, and more preferably 2:1 and 1:2.

The method of the invention comprises applying to the treated plants or the locus thereof in admixture or separately, a fungicidally effective aggregate amount of compound I and a compound of component II A suitable way of application to the crop plants includes application of a tankmix.

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, germinated or soaked seeds.

The novel combinations are extremely effective on a broad spectrum of phytopathogenic fungi, in particular from the Fungi imperfecti and Oomycetes classes. Some of them have a systemic action and can be used as foliar and soil fungicides.

The fungicidal combinations are of particular interest for controlling a large number of fungi in various crops or their seeds, especially wheat, rye, barley, oats, rice, maize, lawns, cotton, soybeans, coffee, sugarcane, fruit and ornamentals in horticulture and viticulture, and in vegetables such as cucumbers, beans and cucurbits.

The combinations are applied by treating the fungi or the seeds, plants or materials threatened by fungus attack, or the soil with a fungicidally effective amount of the active ingredients.

The agents may be applied before or after infection of the materials, plants or seeds by the fungi.

The novel combinations are particularly useful for controlling the following plant diseases:
*Peronospora tabacina* on tobacco,
*Bremia lactucae* on lettuce,
*Pythium debaryanum* on sugar beet,
*Phytophthora infestans* in potatoes and tomatoes,
*Plasmopara viticola* in grapes.

When applied to the plants the compound I is applied at a rate of 50 to 200 g/ha, particularly 75 to 150 g/ha, e.g. 75, 100, or 125 g/ha, in association with 50 to 1500 g/ha, particularly 60 to 1000 g/ha, e.g. 75 g/ha, 80 g/ha, 100 g/ha, 125 g/ha, 150 g/ha, 175 g/ha 200 g/ha, 300 g/ha, 500 g/ha, or 1000 g/ha of a compound of component II, depending on the class of chemical employed as component II. Where the component II is the compound IIA for example 50 to 200 g a.i./ha is applied in association with the compound 1. Where the component II is the compound IIB for example 50 to 300 g a.i./ha is applied in association with the compound 1. Where the component II is a compound of formula IIC for example 50 to 400 g a.i./ha is applied in association with the compound 1. Where the component II is a compound of formula IID for example 50 to 400 g a.i./ha is applied in association with the compound I. Where the component II is the compound IIE for example 50 to 300 g a.i./ha is applied in association with the compound I.

In agricultural practice the application rates depend on the type of effect desired, and range from 0.02 to 3 kg of active ingredient per hectare.

When the active ingredients are used for treating seed, rates of 0.001 to 50, and preferably from 0.01 to 10 g per kg of seed are generally sufficient.

The invention also provides fungicidal compositions comprising the compound I and a compound of component II.

The composition of the invention may be employed in any conventional form, for example in the form of a twin pack, an instant granulate, a flowable or a wettable powder in combination with agriculturally acceptable adjuvants. Such compositions may be produced in conventional manner, e.g. by mixing the active ingredients with appropriate adjuvants (diluents or solvents and optionally other formulating ingredients such as surfactants).

Suitable carriers and adjuvants may be solid or liquid and correspond to the substances ordinarily employed in formulation technology, such as, e.g. natural or regenerated mineral substances, solvents, dispersants, wetting agents, tackifiers, thickeners, binding agents or fertilizers. Such carriers are for example described in WO 96/22690.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty alkyl sulfate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid adjuvant(s), the active agent consisting of at least the compound of formula I together with a compound of component II, and optionally other active agents, particularly guazatin and fenpiclonil. Concentrate forms of compositions generally contain in between about 2 and 80%, preferably between about 5 and 70% by weight of active agent. Application forms of formulation may for example contain from 0.01 to 20% by weight, preferably from 0.01 to 5% by weight of active agent.

Examples for specific formulations-combination are as disclosed e.g. in WO 96/22690, e.g. for wettable powders, emulsifiable concentrate, dusts, extruder granules, coated granules, suspension concentrate.

Slow Release Capsule Suspension 28 parts of a combination of the compound I and a compound of component II, or of each of these compounds separately, are mixed with 2 parts of an aromatic solvent and 7 parts of toluene diisocyanate/polymethylene-polyphenyl-isocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8–15 microns.

The resulting formulation is applied to seeds as an aqueous suspension in an apparatus suitable for that purpose.

Whereas commercial products will preferably be formulated as concentrates, the end user will normally employ dilute formulations.

BIOLOGICAL EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S.R. "Calculating synergistic and antagonistic responses of herbicide combination". Weeds, Vol. 15, pages 20–22; 1967):

ppm=milligrams of active ingredient (=a.i.) per liter of spray mixture $X$=% action by active ingredient I using p ppm of active ingredient $Y$=% action by active ingredient II using q ppm of active ingredient.

According to Colby, the expected (additive) action of active ingredients 1+11 using p+q ppm of active ingredient is $$E = X + Y - \frac{X \cdot Y}{100}$$

If the action actually observed (O) is greater than the expected action (E), then the action of the combination is superadditive, i.e. there is a synergistic effect.

Alternatively the synergistic action may also be determined from the dose response curves according to the so-called WADLEY method. With this method the efficacy of the a.i. is determined by comparing the degree of fungal attack on treated plants with that on untreated, similarly inoculated and incubated check plants. Each a.i. is tested at 4 to 5 concentrations. The dose response curves are used to establish the EC90 (i.e. concentration of a.i. providing 90% disease control) of the single compounds as well as of the combinations ($EC90_{observed}$). The thus experimentally found values of the mixtures at a given weight ratio are compared with the values that would have been found were only a complementary efficacy of the components was present (EC 90 $(A+B)_{expected}$). The EC90 $(A+B)_{expected}$ is calculated according to Wadley (Levi et al., EPPO-Bulletin 16, 1986, 651–657):

$$EC90(A+B)_{expected} + \frac{a+b}{\frac{a}{EC90(A)_{observed}} + \frac{b}{EC90(B)_{observed}}}$$

wherein a and b are the weight ratios of the compounds A and B in the mixture and the indexes (A), (B), (A+B) refer to the observed EC 90 values of the compounds A, B or the given combination A+B thereof. The ratio EC90 $(A+B)_{expected}$/EC90 $(A+B)_{observed}$ expresses the factor of interaction (F). In case of synergism, F is >1.

Example B-1

Action Against *Plasmopara viticola* on Grape

Vine seedlings of the Gutedel variety are grown under greenhouse conditions at 20° C. in standard soil for 5 weeks. Disks 10 mm in diameter are then cut from the leaves. The leaf segments are placed on Petri dishes with their upper side facing downwards. The dishes contain 2 ml of 0.2% water agar. The fungicides are added to demineralised water and diluted appropriately. The fungicidal treatment is carried out one day before the inoculation. The entire leaf surface disk is then uniformly sprayed to drip point with a freshly prepared sporangia suspension (60000/ml) of *Plasmopara viticola*. The leaf discs were incubated for 6 days at 18° C. and a 75% relative humidity with artificial daylight of 16 hours' duration (3000 lux). Evaluation of the infestation is then carried out.

The percentage leaf infestation is assessed and the percentage action relative to the control is calculated. The comparison between the percentage action of the mixture R-metalaxyl (>95% by weight)/N-(3'-(1'-chloro-3-methyl 2'-oxopentan))-3,5-dichloro-4-methylbenzamide (IIA) and the mixture metalaxyl (rac)/N-(3'-(1'-chloro-3-methyl 2'-oxopentan))-3,5-dichloro-4-methylbenzamide (IIA) or the mixture R-metalaxyl (>95% by weight)/methyl (E)-2-methoxyimino-[2-(o-tolyloxymethyl)phenyl]acetate (IIB) and the mixture metalaxyl (rac)/methyl (E)-2-methoxyimino-[2-(o-tolyloxymethyl)phenyl]acetate gives the comparison factor.

Results:

a) I/IIA

| R-metalaxyl >95% by wt. or metalaxyl (racemate) mg a.i./l | IIA mg a.i./l | Mixing ratio I:II | Activity of R-metalaxyl (95%)/IIA % | Activity of metalaxyl (rac)/IIA % | Comparison factor |
|---|---|---|---|---|---|
| 0.1 | 0.05 | 2:1 | 12 | 4 | 3.0 |
| 0.25 | 0.05 | 5:1 | 44 | 2 | 22.0 |
| 0.5 | 0.05 | 10:1 | 41 | 7 | 6.0 | b) I/IIB

| R-metalaxyl >95% by wt. or metalaxyl (racemate) mg a.i./l | IIB mg a.i./l | Mixing ratio I:II | Activity of R-metalaxyl (95%)/IIB % | Activity of metalaxyl (rac)/IIB % | Comparison factor |
|---|---|---|---|---|---|
| 0.1 | 0.1 | 1:1 | 5 | 2 | 2.5 |
| 0.25 | 0.05 | 5:1 | 10 | 4 | 2.5 |
| 0.5 | 0.05 | 10:1 | 31 | 2 | 15.5 |
| 1.0 | 0.25 | 4:1 | 42 | 19 | 2.2 |

Example B-2

Activity Against *Phytophthora infestans* in Tomatoes a) Curative Action

Tomato plants cv. "Roter Gnom" are grown for three weeks and then sprayed with a zoospore suspension of the fungus and incubated in a cabin at 18 to 20° C. and saturated atmospheric humidity. The humidification is interrupted after 24 hours. After the plants have dried, they are sprayed with a mixture which comprises the active ingredients formulated as a wettable powder at a concentration of 200 ppm. After the spray coating has dried, the plants are returned to the humid chamber for 4 days. Number and size of the typical foliar lesions which have appeared after this time are used as a scale for assessing the efficacy of the test substances.

b) Preventive-Systemic Action

The active ingredients which are formulated as a wettable powder is introduced, at a concentration of 60 ppm (relative to the soil volume), onto the soil surface of three-week-old tomato plants cv. "Roter Gnom" in pots. After an interval of three days, the underside of the leaves is sprayed with a zoospore suspension of *Phytophthora infestans*. They are then kept for 5 days in a spray cabin at 18 to 20° C. and saturated atmospheric humidity. After this time, typical foliar lesions appear whose number and size are used for assessing the efficacy of the test substances.

Example B-3

Activity Against *Phytophthora* in Potato Plants a) Residual-Protective Action

2–3 week old potato plants (Bintje variety) are grown for 3 weeks and then sprayed with a spray mixture (0.02% of active ingredients) prepared with a wettable powder of the active ingredients mixture. After 24 hours, the treated plants are infected with a sporangia suspension of the fungus. The fungus infestation is assessed after the infected plants have been incubated for 5 days at a relative atmospheric humidity of 90–100% and 20° C.

b) Systemic Action

A spray mixture (0.002% of active ingredients based on the soil volume) prepared with a wettable powder of the active ingredients mixture is poured next to 2–3 week old potato plants (Bintje variety) which have been grown for 3 weeks. Care is taken that the spray mixture does not come into contact with the aerial parts of the plants. After 48 hours, the treated plants are infected with a sporangia suspension of the fungus. Fungus infestation is assessed after the infected plants have been incubated for 5 days at a relative atmospheric humidity of 90–100% and 20° C.

The efficacy of the test combinations and the single active ingredients in the above tests is determined by comparing the degree of fungal attack with that on untreated, similarly inoculated check plants.

Example B-4

Activity Against *Pythium debaryanum* on Sugar Beet

The fungus is cultured from sterile oat grains and added to a soil/sand mixture. The soil thus infected is introduced into flowerpots and sown with sugar beets seeds. Immediately after sowing, the test preparations, formulated as wettable powders, are poured over the soil as an aqueous suspension (20 ppm of active ingredients based on the soil volume). The pots are then placed in a greenhouse at 20–24° C. for 2–3 weeks. The soil is constantly kept uniformly moist by gentle spraying with water. For evaluation of the tests, the emergence of the sugar beets plants and the proportion of healthy and sick plants are determined. After treatment with the active ingredients mixtures I+IIA–I+IIE, more than 80% of the plants emerge and have a healthy appearance. In the control pots, only isolated emerged plants with a sickly appearance are observed.

Example B-5

Action Against *Peronospora tabacina*

Formulated active ingredients mixtures I+IIA–I+IIE in a range of concentrations (10, 1, 0.1 ppm) are mixed with agar prepared with water, and the agar mixture is poured into Petri dishes. After cooling, 100 µl of a sporangia suspension ($10^6$ spores/ml) are streaked onto the plate. The plates are incubated for 16 hours at 18° C.

The mixtures I+IIA–I+IIE were not found to inhibit the germination of *Peronospora tabacina*.

The mixtures according to the invention exhibit good activity in these Examples.

What is claimed is:

1. A method of combating phytopathogenic diseases on crop plants which comprises applying to the crop plants or the locus thereof being infested with said phytopathogenic disease an effective amount of a combination of a first component I metalaxyl having an R-enantiomer content of more than 95% by weight, in association with a second component II, methyl (E)-2-methoxyimino-[2-(o-tolyloxymethyl)phenyl]acetate, wherein components I and II are applied in a quantity producing a synergistic phytopathogenic disease controlling effect.

2. A method according to claim 1 wherein the phytopathogenic disease is caused by Oomycetes.

3. A method according to claim 1 wherein the components I and II are applied in a quantity producing a synergistic disease controlling effect, being in a weight ratio of component I to component II between 10:1 to 1:10.

* * * * *